United States Patent [19]
Saito

[11] Patent Number: 5,948,358
[45] Date of Patent: Sep. 7, 1999

[54] WASHING DEVICE FOR AUTOMATIC BIOCHEMICAL ANALYZER

[75] Inventor: Shin Saito, Tokyo, Japan

[73] Assignee: Jeol Ltd., Tokyo, Japan

[21] Appl. No.: 08/915,901

[22] Filed: Aug. 21, 1997

[51] Int. Cl.$^6$ .............................. G01N 35/10; B08B 9/02
[52] U.S. Cl. .............................. 422/64; 422/81; 422/100; 436/43; 436/49; 436/54; 436/180; 134/169 R; 134/170
[58] Field of Search .................................. 422/63, 64, 99, 422/100, 81; 436/43, 47, 49, 54, 174, 180; 134/21, 22.11, 22.12, 24, 37, 169 R, 170; 141/130; 73/864.01

[56] References Cited

U.S. PATENT DOCUMENTS

| | | | |
|---|---|---|---|
| 3,836,329 | 9/1974 | Jordan | 134/21 |
| 3,849,830 | 11/1974 | Wagner | 134/21 |
| 4,227,886 | 10/1980 | Bullock et al. | 422/67 |
| 5,730,938 | 3/1998 | Carbonari et al. | 422/64 |

FOREIGN PATENT DOCUMENTS

5-2024  8/1993  Japan .

*Primary Examiner*—Long V. Le
*Attorney, Agent, or Firm*—Webb Ziesenheim Logsdon Orkin & Hanson, P.C.

[57] ABSTRACT

There is disclosed a washing device for use with an automatic biochemical analyzer using reaction containers. The washing device comprises a sucking portion and a draining tube. When the sucking portion is advanced into any one reaction container placed in position and is set in a given position, a communication passage is created between the inner wall surface of the container and the outer wall surface of the sucking portion and between the bottom surface of the container and the bottom surface of the sucking portion. During draining, the container is depleted of wash liquid. Outside air flows from the communication passage into the container through its opening at the top end at a flow rate more than a given value. The air flow blows away the water droplets adhering to the inner wall surface of the container. The blown water droplets are urged downward toward the sucking port in the suction portion. Then, the water droplets are discharged into a waste tank through the draining tube. Thus, the water droplets can be easily and almost completely removed.

4 Claims, 6 Drawing Sheets

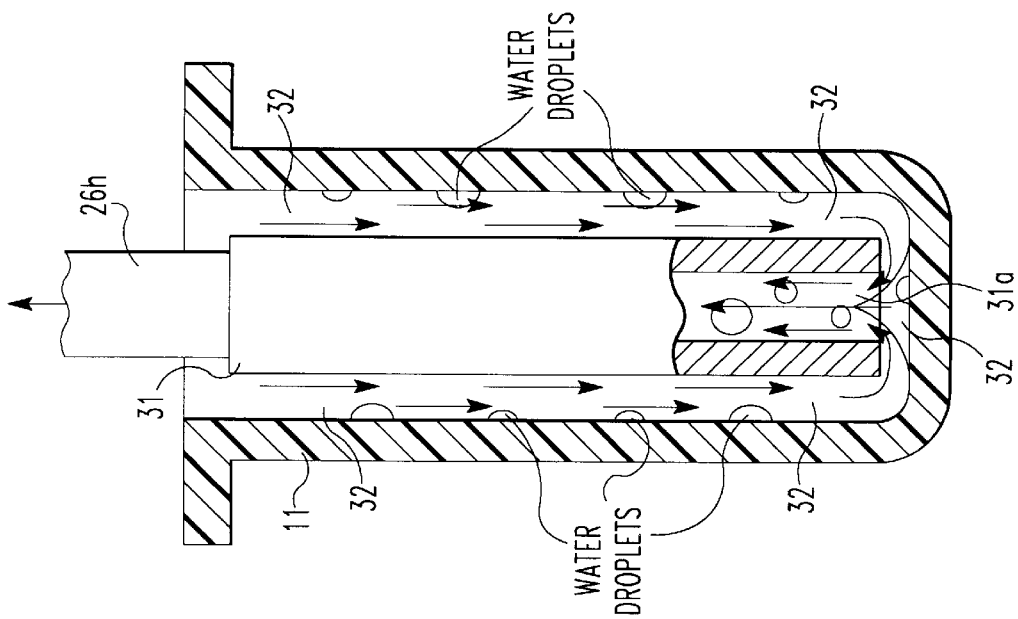
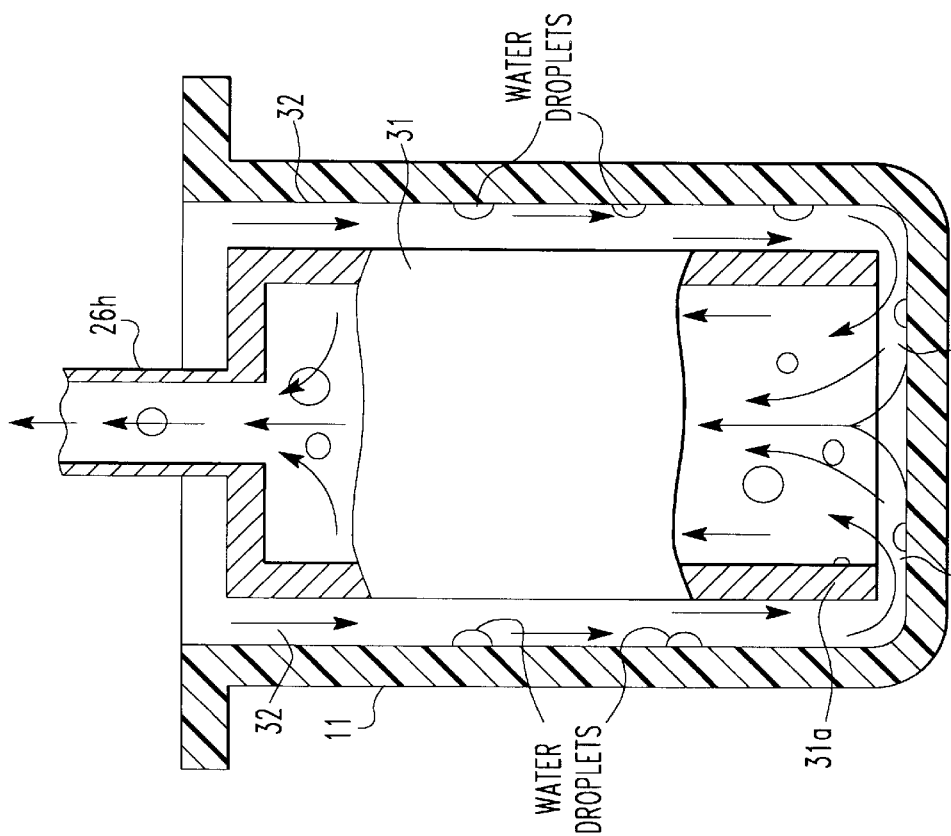

WASHING DEVICE FOR AUTOMATIC BIOCHEMICAL ANALYZER

FIELD OF THE INVENTION

The present invention relates to an automatic biochemical analyzer for analyzing biological samples such as blood and urine in terms of plural items and, more particularly, to a washing device for washing reaction containers holding aliquots of sample or reagent after detection.

BACKGROUND OF THE INVENTION

Such automatic biochemical analyzers for analyzing biological samples have been known, as proposed in Japanese Patent Laid-Open No. 2024/1993. In this prior art technique, a plurality of sample containers are set on a sample disk. In this instrument, aliquots of sample in the sample containers set on the sample disk are drawn in by a sample pipette and dispensed into reaction containers on a reaction disk. A reagent pipette draws in reagents from plural reagent disks and adds the reagents to the aliquots of sample. Thus, the sample is analyzed in terms of plural items. During the analysis, the order in which the items are analyzed is determined, taking account of the time required for the processing, in order to shorten this processing time.

In this automatic biochemical analyzer, a biological sample is reacted with plural reagents within reaction containers on the reaction turntable, and the reaction products are detected by detectors. Upon completion of the detection, each reaction container is sent to a washing location at which the container is washed by a washing device.

This washing operation starts with discharging the biological sample and the reagents from the reaction container. Then, the interior of the reaction container is washed a few times or several times with an alkaline detergent, an acidic detergent, or pure water. Finally, the interior of the reaction container is washed with pure water. The wash water is drained off, thus completing the washing of the reaction container. This washed reaction container is reused for measurement of the next biological sample unless the container is heavily contaminated.

The final stage of washing with pure water has been heretofore done by a washing device as shown in FIG. 6. This washing device comprises a relatively thin draining tube 24 and a thin-walled sucking portion 25 in the form of a block. The sucking portion 25 is mounted at the front end of the draining tube 24. An X-shaped groove 25a is formed in the bottom surface of the sucking portion 25. This groove 25a is in communication with the hole inside the draining tube 24.

In the operation of this conventional washing device, the sucking portion 25 is put into a reaction container 11 and made to abut against the inner bottom of the reaction container 11 or kept slightly afloat. When a draining pump (not shown) draws in fluid through the draining tube 24, the wash water in the reaction container 11 is drawn in from the sucking portion 25 and discharged into a draining tank (not shown) via the draining tube 24. When the wash water in the reaction container 11 is almost fully drained away, some droplets of the wash water may remain and adhere to the inner bottom and inner side wall of the reaction container 11. In this case, if next biological sample and reagents are injected into this reaction container 11, these biological sample and reagents might be affected by the remaining water droplets.

Accordingly, if the operator subsequently attempts to remove the remaining water droplets completely by the drawing action of the sucking portion 25, the water droplets adhering to the inner bottom of the reaction container 11 are attracted but the water droplets adhering to the inner side wall are hardly attracted. Therefore, it is quite difficult for the prior art washing device to remove water droplets adhering to the inner side wall of the reaction container.

SUMMARY OF THE INVENTION

In view of the foregoing, the present invention has been made.

It is an object of the present invention to provide a washing device which is for use with an automatic biochemical analyzer and which can easily and certainly remove water droplets from the inner side walls of reaction containers.

This object is achieved by a washing device comprising a draining tube for drawing in fluid by a reduced pressure and a sucking portion mounted at the front end of the draining tube. This washing device is adapted for use with an automatic biochemical analyzer comprising an array of reaction containers. The washing device is disposed around the biochemical analyzer. A given amount of sample and a given amount of reagent are reacted within each reaction container having an inner bottom surface. The reaction products are detected. Then, the washing device washes the reaction container. The sucking portion of the washing device can be advanced into the reaction container. The sucking portion has an opening that is close and opposite to the inner bottom surface of the reaction container. Under this condition, a communication passage is formed which consists of a substantially uniform gap between the inner wall surface of the reaction container and the outer surface of the sucking portion. When fluid is being drawn in through the opening to drain away liquid, if the communication passage is depleted of the wash liquid, an air flow is created in the communication passage. This air flow has a flow rate sufficient to blow away droplets of the wash liquid adhering to the inner surface of the reaction container. As a result, the liquid droplets are drawn off through the draining tube.

Other objects and features of the invention will appear in the course of the description thereof, which follows.

BRIEF DESCRIPTION OF THE DRAWINGS

FIG. 5(a) is a front elevation partially in cross section of the washing device shown in FIGS. 4(a) and 4(b), illustrating the operation of the washing device;

FIG. 5(b) is a side elevation taken from the right side of the device shown in FIG. 5(a)

DETAILED DESCRIPTION OF THE INVENTION

Figure 1:
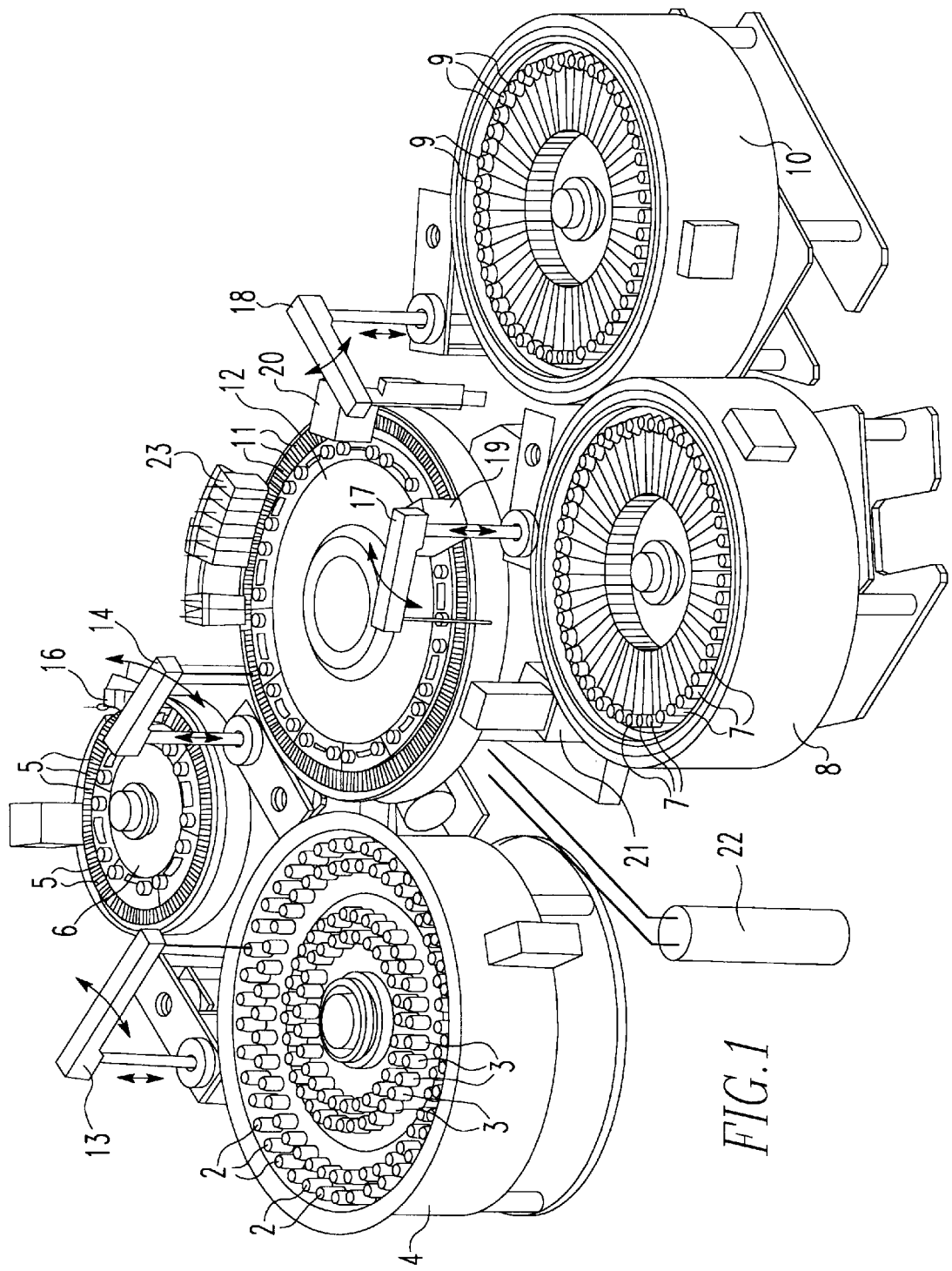
FIG. 1 is a perspective view of an automatic biochemical analyzer equipped with a washing device in accordance with the present invention.

The whole structure of an automatic biochemical analyzer equipped with a washing device in accordance with the present invention is shown in FIG. 1. The biochemical analyzer, generally indicated by reference numeral 1, comprises a sample turntable 4, a diluting turntable 6, a f first reagent turntable 8, a second reagent turntable 10, and a reaction turntable 12. A given number of sample containers 2 holding biological samples are set on the sample turntable 4. The samples are drawn from the sample containers 2 and diluted. The diluted samples are put in diluting containers 5, which in turn are set on the diluting turntable 6. Reagent containers 7 holding first and fourth reagents of different kinds are set on the reagent turntable B. Reagent containers 9 holding second and third reagents of different kinds are set on the second reagent turntable 10. A given number of reaction containers 11 are set on the reaction turntable 12.

On the sample turntable 4, the sample containers 2 are arranged in two rows and regularly spaced from each other by one pitch. Each row consists of 42 sample containers 2. This sample turntable 4 is rotated incrementally, one pitch at a time.

A diluting pipette 13 is mounted between the sample turntable 4 and the diluting turntable 6 and reciprocated between the sample turntable 4 and the diluting turntable 6 by a drive mechanism (not shown). The diluting pipette 13 is moved up and down for aspirating and injecting operations. When the diluting pipette 13 gains access to one sample container 2 in a given location on the sample turntable 4, a sampling pump (not shown) is operated to take in a given amount of sample. Then, the diluting pipette 13 obtains access to one diluting container 5 in a given position on the diluting turntable 6. A given amount of diluent (normally physiological salt solution) supplied from the diluting pipette 13 itself is injected into the diluting container 5, along with the sample. As a result, the sample is diluted by a given factor within the diluting container 5. Thereafter, the diluting pipette 13 is washed by a washing device (not shown) located at the midway location in the reciprocating stroke of the pipette.

A sampling pipette 14, a stirring device 15, and a washing device 16 are mounted around the diluting turntable 6, as well as the diluting pipette 13. The diluted sample in the diluting container 5 is stirred by the stirring device 15, thus producing a uniform diluted sample. Let N be the number of the diluting containers 5 circumferentially arranged on the diluting turntable 6. The diluting turntable 6 is rotated incrementally, M pitches at a time. To arrange these devices 13, 14, 15, and 16 with sufficient degrees of freedom, M and N are selected as not to have any common factor.

A drive mechanism (not shown) reciprocates the sampling pipette 14 between the diluting turntable 6 and the reaction turntable 12 through the dilution washing device 16. When the sampling pipette 14 is lowered to gain access to one diluting container 5 in a given position on the diluting turntable 6, a diluting sampling pump (not shown) is operated to drawn in a given amount of diluted sample. Then, the sampling pipette 14 is lowered to obtain access to one reaction container 11 in a given position on the reaction turntable 12, and the pipette 14 injects the drawn diluted sample into the reaction container 11.

The stirring device 15 is moved up and down by a vertical driving mechanism (not shown) and has a stirring rod (not shown) reciprocating diametrically of the diluting turntable 6. The stirring rod of the diluting turntable 6 advances into a diluted sample in the diluting container 5 and moves back and forth to produce a uniform diluted sample. The washing device 16 cleanses the sampling pipette 14 after the diluted sample is injected into the reaction container 11.

Disposed around the reaction turntable 12 are reagent pipettes 17, 18, stirring devices 19, 20, a multi-wavelength photometer 21 acting as a detector, a thermostatic chamber 22, and a washing device 23 for washing the reaction container, as well as the sampling pipette 14. These devices operate at their respective positions relative to the reaction container 11.

Figure 2:
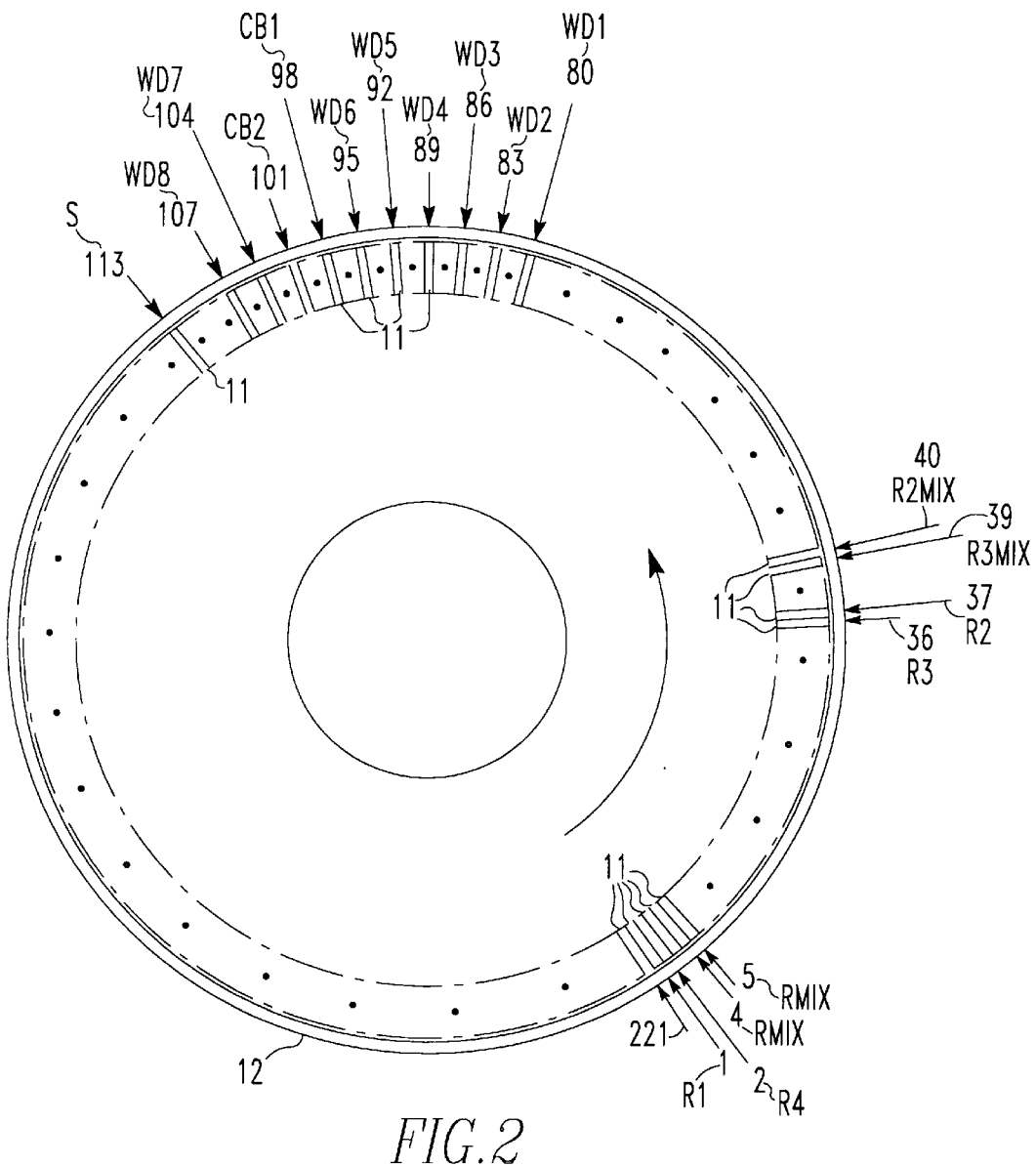
FIG. 2 is a top plan view of a reaction turntable used in the washing device shown in FIG. 1, illustrating various operation positions.

Referring to FIG. 2, it is assumed that 221 reaction containers 11 are disposed along the whole outer periphery of the reaction turntable 12. Numerals 1 through 221 are given to 221 positions taken in a counterclockwise direction along the outer surface of the reaction turntable 12. A first reagent is injected at position 1. A fourth reagent is injected at position 2. The first reagent is stirred at position 4. The fourth reagent is stirred at position 5. A third reagent is injected at position 36. A second reagent is injected at position 37. The third reagent is stirred at position 39. The second reagent is stirred at position 40. The reaction container 11 is washed and checked for contamination at positions 80–107. A diluted sample is injected at position 113. The pipettes 14, 17, 18, the stirring devices 19, 20, and the washing device 23 perform their operations on the reaction container 11 halted at the positions described above.

The reagent pipette 17 is reciprocated between the reaction turntable 12 and the reagent turntable 8 by a driving mechanism (not shown). When the first reagent should be pipetted into the reaction container 11, the reagent pipette 17 is lowered and obtains access to the reagent container 7 located at a given position on the reagent turntable 8. Then, a reagent pump (not shown) is operated to draw in a given amount of reagent. Thereafter, the pipette rotates toward the reaction turntable 12. The pipette is lowered to get access to the reaction container 11 positioned at a given location on the reaction turntable 12. The drawn reagent is injected as the first reagent into the reaction container 11.

The reagent pipette 17 operates similarly when the fourth reagent held in other reagent container 7 is pipetted into the reaction container 11. As mentioned previously, the position at which the fourth reagent is pipetted differs from the position at which the first reagent is pipetted. That is, the reagent pipette 17 is designed so that it can come to a halt at two pipetting positions.

The stirring device 19 is moved up and down by a driving mechanism (not shown) and has a stirring rod (not shown) that is rotated and moved back and forth. The stirring rod is advanced into the reaction container 11 in a given position on the reaction turntable 12 and then rotated and moved back and forth diametrically of the reaction turntable 12. This assures that the first reagent induces a uniform reaction of the diluted sample.

The stirring device 19 similarly stirs the diluted sample and the fourth reagent inside the reaction container 11. As described above, the position at which the fourth reagent is stirred is different from the position at which the first reagent is stirred.

The reagent pipette 18 draws the second or third reagent from the second reagent turntable 10 and injects the drawn reagent into the reaction container located in a given position on the reaction turntable, in exactly the same way as the reagent pipette 17. The stirring device 20 stirs the second or third reagent and the diluted sample in the reaction container, in exactly the same manner as the stirring device 19.

The multi-wavelength photometer 21 measures the absorbance of the diluted sample inside the reaction container 11 and detects the reaction products arising from the diluted sample in the reaction container 11.

The thermostatic chamber 22 maintains constant the temperature of the reaction containers 11 on the reaction turntable 12 at all times.

The washing device 23 uses a draining pump (not shown) to draw in the detected diluted sample and reagent held in the reaction container 11. The drawn sample and reagent are discharged into a draining tank. Then, a detergent pump (not shown) supplies a detergent into this reaction container 11 to wash the interior of the reaction container 11. The detergent is then drawn off into the draining tank. At this time, the degree of contamination of the reaction container 11 is measured. If it is heavily contaminated, a warning is issued to replace the container.

Let N be the number of the reaction containers 11 circumferentially arranged on the reaction turntable 12. This reaction turntable 12 is rotated incrementally, M pitches at a time. To arrange these devices 14, 17, 18, 19, 20, 21, 22, and 23 with sufficient degrees of freedom, M and N are selected as not to have any common factor. The reaction turntable 12 is rotated through more than 180 degrees in one step. In the present embodiment, the 221 reaction containers 11 are rotated in 112 pitches in one step.

Suppose that one reaction container is halted at position 1. This container is rotated in 112 pitches in the next one step and reaches position 113. The container is rotated in 112 pitches in the next one step and arrives at position 4. In summary, after incremental movements in two steps, the container has been moved in 3 pitches.

Figure 3:
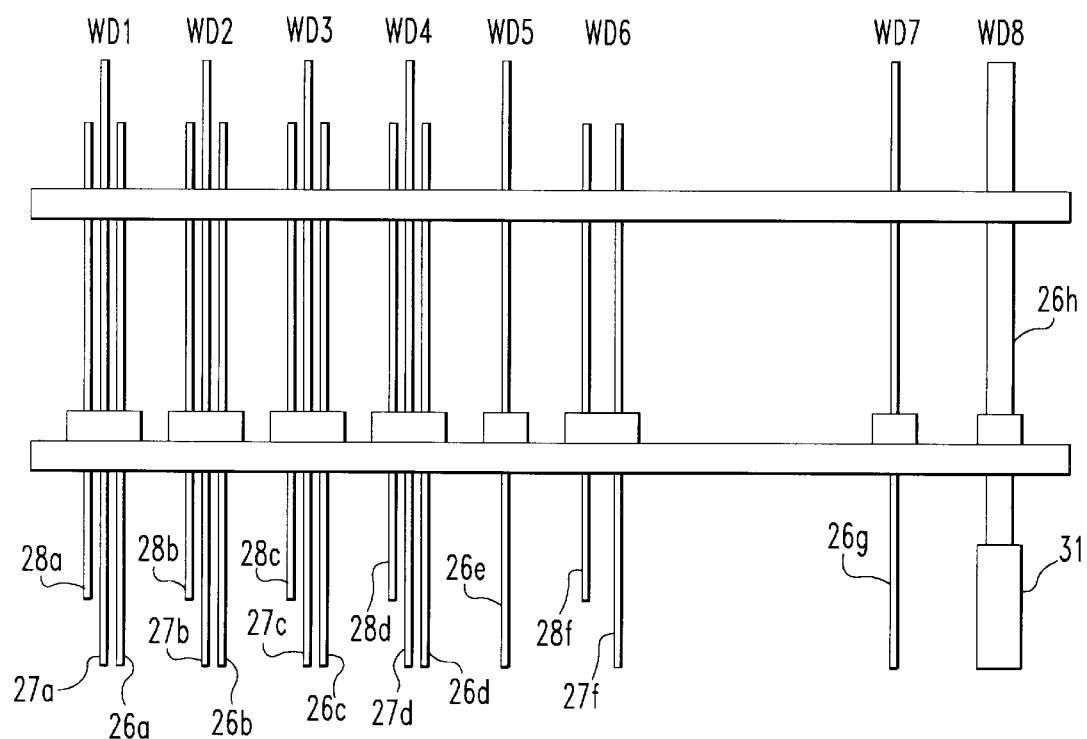
FIG. 3 is a diagram illustrating various washing steps performed by the washing device shown in FIG. 1 to wash one reaction container.

FIG. 3 illustrates a washing operation performed by the washing device 23 of the present embodiment. A first washing step WD1 is performed at position 80. In particular, a mixture of a diluted sample and a first or fourth reagent in the reaction container 11 is drawn in by the draining pump (not shown) via a draining tube 26a and drawn off.

Then, a given amount of wash water including an alkaline detergent is injected in to the reaction container 11 through a water feed tube 27a. If the supplied wash water is excessive and overflows, the excess water is discharged into the draining tank via an overflow tube 28a. Consequently, the wash water is prevented from overflowing the reaction container 11; otherwise the surroundings of the container 11 would be contaminated. Upon completion of the washing of the reaction container 11, the wash water is drawn through the draining tube 26a and drained off.

Then, this reaction container 11 is rotated in two steps and arrives at position 83, where a second washing step WD2 is carried out. A given amount of wash water containing an acidic detergent is injected into the container 11 through a water feed tube 27b. If the wash water overflows, the excess water is drained off into the draining tank via an overflow tube 28b in the same way as in the above-described case. When the washing of the reaction container 11 ends, the wash water is drawn through the draining tube 26b and drained off.

This reaction container 11 is rotated in two steps and reaches position 86, where a third washing step WD3 is effected. A given amount of pure water is injected into the reaction container 11 via a water feed tube 27c. If the pure water overflows, the excess pure water is drawn off into the draining tank through an overflow tube 28c in the same way as in the foregoing. When this washing step ends, the pure water is drawn through a draining tube 26c and discharged.

Thereafter, the reaction container 11 is rotated in two steps and arrives at position 89, where a fourth washing step WD4 is carried out. At this time, a given amount of pure water is fed into the container 11 via a water feed tube 27d. If the pure water overflows, the excess water is drained off into the draining tank via an overflow tube 28d in the same way as the foregoing. When this washing step ends, the pure water is drawn through a draining tube 26d and drained off.

Then, this reaction container 11 is rotated in two steps and reaches position 92, where a fifth washing step WD5 is carried out. In particular, water remaining in the container 11 is aspirated through a draining tube 26e and drained off.

Thereafter, the reaction container 11 is rotated in two steps and arrives at position 95, where a sixth washing step WD6 is carried out. A given amount of pure water is supplied into the reaction container 11 by way of a wafer feed tube 27f. If the pure water overflows, the excess pure water is discharged into the draining tank via an overflow tube 28f in the same way as in the foregoing step.

Under this condition, the reaction container 11 is moved into 11 is measured (measuring step CB1). Then, the container 11 is moved into position 101, where the level of contamination of the reaction container 11 is again measured (measuring step CB2). If the container is found to be heavily contaminated, the container 11 is replaced with a new one.

The reaction container 4 is then rotated in four steps and arrives at position 104, where a seventh washing step WD7 is carried out. The pure water in the container 11 is aspirated and drained off via a draining tube 26g.

Figure 4A:
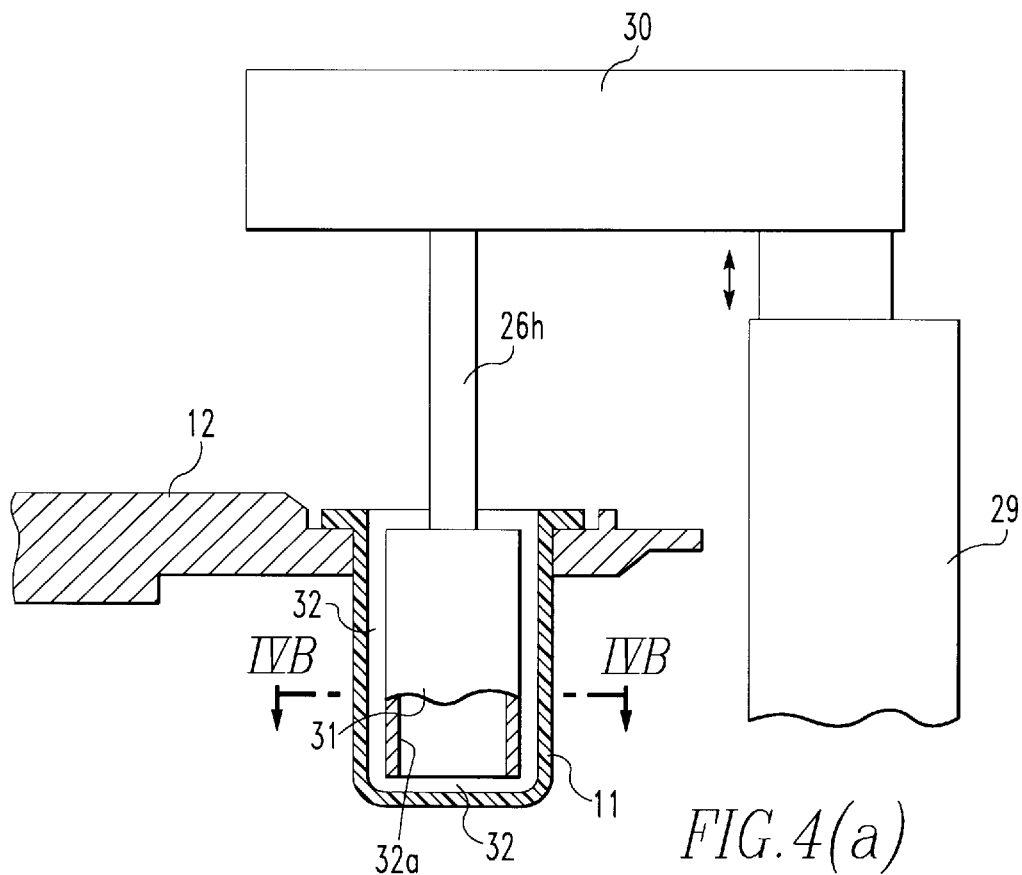
FIG. 4(a) is a side elevation partially in cross section of a washing device in accordance with the invention, and in which the sucking portion of the washing device is placed in position within a reaction container.

Finally, the reaction container 11 is rotated in two steps and reaches position 107, where an eighth washing step WD8 is performed. The pure water in the container 11 is drawn through a draining tube 26h and discharged. This eighth washing step WD8 is done by a washing device comprising a support base 29 and an arm 30 held to the support base 29 so as to be movable up and down, as shown in FIG. 4(a). The draining tube 26h is held to this arm 30. A sucking portion 31 is held to the bottom end of the draining tube 26h.

Figure 4B:
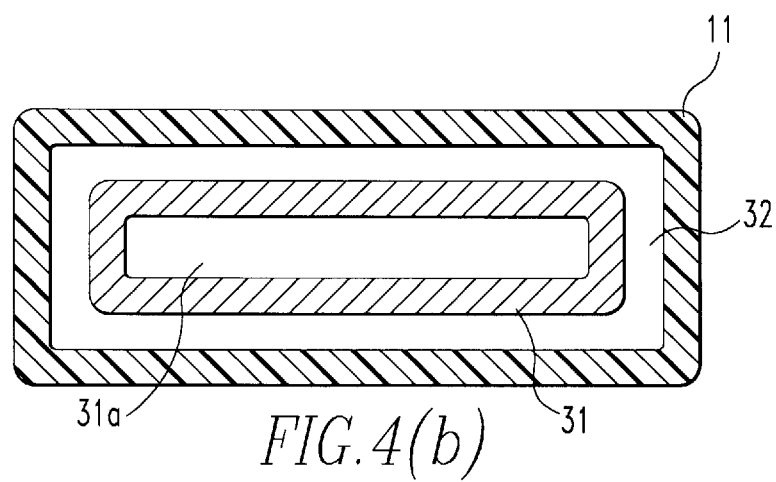
FIG. 4(b) is a cross-sectional view taken on line IVB-IVB of FIG. 4(a)
Figure 6:
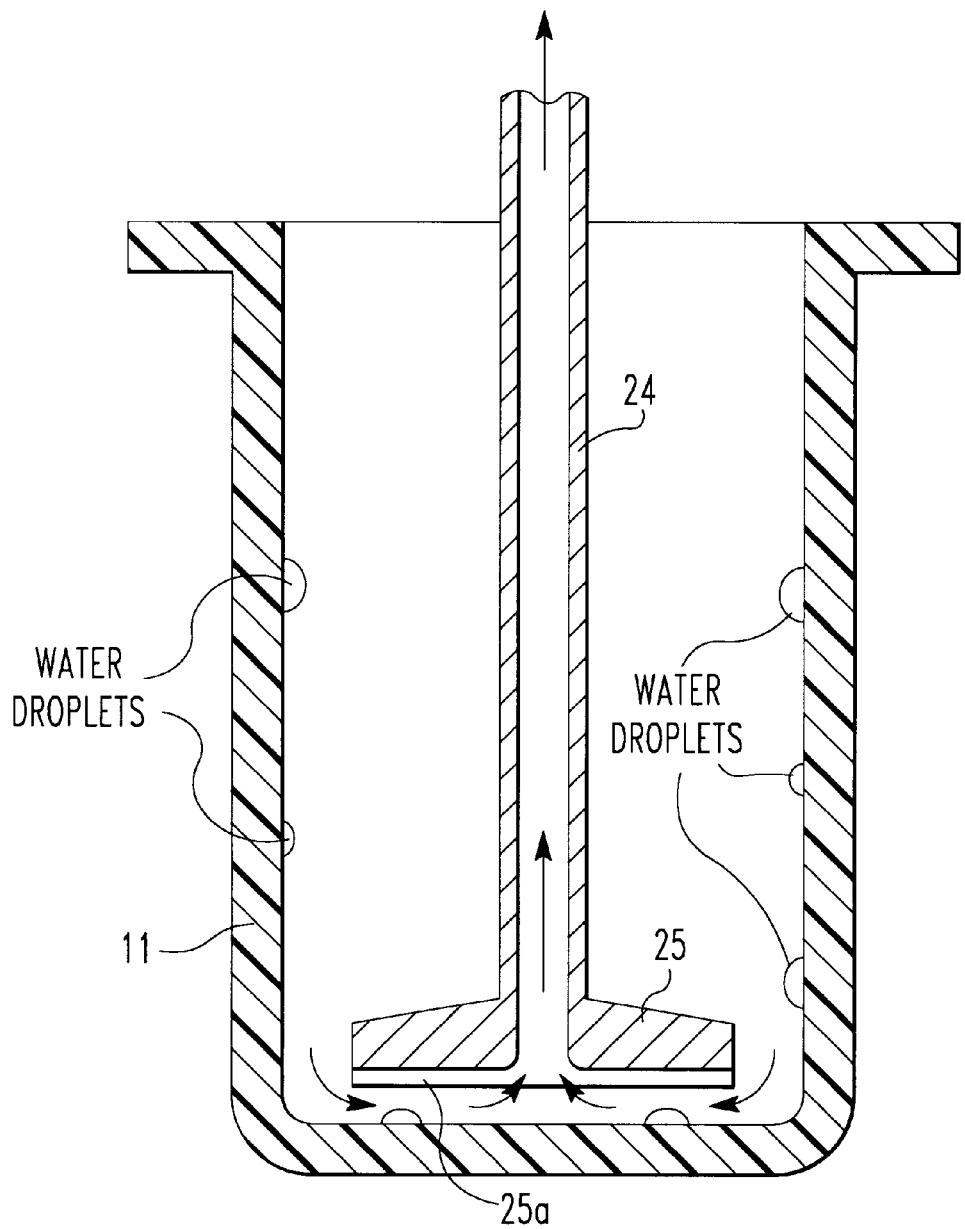
FIG. 6 is a cross-sectional view of the prior art washing device, illustrating the operation.

This sucking portion 31 assumes a relatively flat boxlike form whose top end is closed off and whose bottom end is open. The thickness and the width of the sucking portion 31 are so set that the sucking portion can enter the reaction container 11. The height of the sucking portion 11 is substantially equal to the depth of the space inside the container 11. When this sucking portion 31 enters the container 11 and is placed in position, a relatively small gap is created between the inner wall surface of the container 11 and the outer wall surface of the sucking portion 31 and between the inner bottom surface of the container 11 and the outer bottom surface of the sucking portion 31. This gap forms a communication passage 32 that places the opening at the top of the container 11 in communication with the opening at the bottom of the sucking portion 31. As shown in FIG. 4(b), the cross-sectional area of this communication passage 32 between the inner wall surface of the reaction container 11 and the outer wall surface of the sucking portion 31 is set equal to the cross-sectional area of a hole 31a inside the sucking portion 31. It is not always necessary that these two cross-sectional areas be equal. They may be different. However, the cross-sectional area of the hole 31a in the sucking portion 31 is preferably set larger than that of the communication passage 32 in order that the air flow rate in the communication passage 32 be larger for the same amount of aspirated air. If the cross-sectional area of the hole 31a is set larger than that of the communication passage 32, fluid flows through the communication passage 32 at a higher rate than through the inner hole 31a. The cross-sectional area of the hole inside the draining tube 26h is larger than conventional and more than the cross-sectional area of the hole 31a in the sucking portion 31.

In the present example of washing device constructed in this way, the following eighth washing step WD8 is carried out for the reaction container 11 halted at position 107. First, the arm 30 is lowered to move the draining tube 26h and the sucking portion 31, so that the sucking portion 31 advances into the reaction container 11. When the space between the bottom end of the sucking portion 31 and the bottom surface of the reaction container 11 assumes a given value, the downward movement of the arm 30 stops, and the sucking portion 31 is halted there.

Under this condition, the communication passage 32 is created between the inner wall surface of the container 11 and the outer wall surface of the sucking portion 31 and between the inner bottom surface of the container 11 and the outer bottom surface of the sucking portion 31. The draining pump (not shown) connected with the draining tube 26h is driven. As a result, wash water consisting of pure water in the reaction container 11 is drawn into the sucking portion 31 and sent into a waste tank (not shown) through the draining tube 26h. At this time, the wash water smoothly flows downwardly through the communication passage 32 toward the sucking port in the sucking portion 31.

When the interior of the reaction container 11 is almost fully depleted of the wash water, droplets of the wash water adhere to the inner wall surface of the container 11 and to the bottom surface. However, when outside air is started to be aspirated from the sucking portion 31, the air flows in from the opening at the top end of the reaction container 11, as shown in FIGS. 5(a) and 5(b), and passes through the communication passage 32 into the sucking portion 31. The flow rate of air flowing through the communication passage 32 is considerably high and in excess of a given value. Therefore, the water droplets adhering to the inner wall of the reaction container 11 are blown away by the air flowing at such a high flow rate. The water droplets are moved downward toward the suction port in the sucking portion 31, along with the air. Then, they are conveyed into the waste tank through the draining tube 26h from the sucking portion 31. In this way, the reaction container 11 is washed by the eighth washing step WD8. As a result of this washing step, the water droplets can be almost fully removed from the inner wall of the container 11.

It is necessary that the flow rate of air through the communication passage 32 be large enough to blow away the water droplets adhering to the inner wall of the container toward the bottom surface of the container by the flowing air. For this purpose, it is necessary to appropriately select the combination of the magnitude of a negative pressure inside the draining tube 26h and the cross-sectional area determining the fluid channel resistance of the communication passage 32.

As can be understood from the description provided thus far, in a washing device in accordance with the present invention, when a reaction container is washed, a communication passage is created between the inner surface of the container and the outer surface of a sucking portion. The communication passage extends from the opening at the top of the container to the bottom surface. Thus, an air flow having a large flow rate is created. Therefore, water droplets adhering to the inner wall surface of the reaction container can be almost completely removed. Consequently, the container can be cleaned with greater certainty. Furthermore, it suffices to form the sucking portion along the interior geometry of the reaction container. Hence, the structure of the washing device can be made simpler. Also, the washing device can be fabricated economically.

What is claimed is:

1. A washing device for use with an automatic biochemical analyzer having an array of reaction containers having a top opening with a rim thereabout and having substantially identical spaces inside thereof, said washing device comprising:

a draining tube having an end connectable to a vacuum pump for acting to suck fluid by a reduced pressure;

a sucking portion connected to said draining tube and capable of advancing into the space inside of any one of the reaction containers placed in position for washing, said sucking portion having a solid elongate wall with exterior surfaces and an opening with a rim thereabout, said opening being in communication with a space inside said reaction container when placed in position for washing, said space terminating at a bottom surface of said reaction container; and the exterior surfaces of the sucking portion when inserted in a reaction container in position for washing defining a communication passage consisting of a substantially uniform gap created between inner surfaces of said reaction container and outer surfaces of said sucking portion along the substantially entire length of the inner surfaces between the rim of the reaction container and the rim of the sucking portion, said communication passage opening to the atmosphere near the rim of the reaction container confining an air flow created by the reduced pressure in said draining tube having a flow rate sufficient to blow away liquid droplets adhering to the inner surfaces of said container by air drawn in from said opening when said communication passage is depleted of wash liquid, said liquid droplets blown away being drawn off via said draining tube.

2. A washing device for use with an automatic biochemical analyzer having an array of reaction containers having a top opening with a rim thereabout and having substantially identical inner spaces, said washing device comprising:

a draining tube having an end connectable to a vacuum pump and acting to suck fluid by a reduced pressure;

a sucking portion connected to said draining tube and capable of advancing into the inner space of any one of the reaction containers placed in position for washing, said sucking portion having a solid elongate wall with exterior surfaces and an opening with a rim thereabout in communication with a space inside said reaction container when placed in position, said space terminating at a bottom surface of said reaction container, said sucking portion being capable of advancing into any one of said reaction containers placed in position through said top opening in said reaction container from outside, said sucking portion having an external contour spaced from and conforming to geometry of a space inside said reaction container;

said external contour of said sucking portion being so designed that when said sucking portion is placed in position within said reaction container, a communication passage is created by a substantially uniform gap between said reaction container and said sucking portion along the substantially entire length of the container between the rim of the reaction container to the rim of the sucking portion, said communication passage opening to the atmosphere along the rim of the reaction container; and said communication passage creating an air flow having a flow rate sufficient to blow away liquid droplets adhering to the inner surfaces of said container by air drawn in from said opening when said communication passage is depleted of wash liquid, said liquid droplets blown away being drawn off via said draining tube.

3. The washing device of claim 1 or 2, wherein said communication passage and said opening in said sucking portion are substantially equal in cross-sectional area.

4. The washing device of claim 1 or 2, wherein said draining tube is larger than said communication passage.

* * * * *

UNITED STATES PATENT AND TRADEMARK OFFICE
CERTIFICATE OF CORRECTION

PATENT NO. : 5,948,358
DATED : September 7, 1999
INVENTOR(S) : Shin Saito

It is certified that error appears in the above-identified patent and that said Letters Patent is hereby corrected as shown below:

Title Page, refer to [73] Assignee, "Jeol Ltd." should read
    --JEOL Ltd.--.

Title Page, insert:
    --[30] Foreign Application Priority Data
        Aug. 21, 1996 [JP]   Japan ............8-219740--.

Column 3 Line 7 "a f first" should read --a first--.

Column 3 Line 15 "turntable B." should read
    --turntable 8.--.

Column 3 Line 59 "to drawn" should read --to draw--.

Column 6 Line 20 after "moved into" insert --98 and--.

Signed and Sealed this

Twenty-fifth Day of July, 2000

Attest:

Q. TODD DICKINSON

*Attesting Officer*     *Director of Patents and Trademarks*